(12) United States Patent
Scott et al.

(10) Patent No.: US 8,118,733 B2
(45) Date of Patent: Feb. 21, 2012

(54) HEAT PROTECTION SYSTEMS AND METHODS FOR REMOTE VIEWING DEVICES

(75) Inventors: Joshua L. Scott, Jordan, NY (US); Thomas W. Karpen, Skaneateles, NY (US)

(73) Assignee: GE Inspection Technologies, LP, Skaneateles, NY (US)

( * ) Notice: Subject to any disclaimer, the term of this patent is extended or adjusted under 35 U.S.C. 154(b) by 1460 days.

(21) Appl. No.: 11/644,166

(22) Filed: Dec. 22, 2006

(65) Prior Publication Data

US 2008/0151046 A1 Jun. 26, 2008

(51) Int. Cl.
*A61B 1/00* (2006.01)

(52) U.S. Cl. ........... 600/130; 600/134; 348/65; 348/182

(58) Field of Classification Search .................. 600/132, 600/129, 121, 178, 130, 134; 228/102; 606/85; 250/492.1; 382/152; 348/65, 182
See application file for complete search history.

(56) References Cited

U.S. PATENT DOCUMENTS

| | | | |
|---|---|---|---|
| 4,700,693 A | 10/1987 | Lia et al. |
| 4,727,859 A | 3/1988 | Lia |
| 4,733,937 A | 3/1988 | Lia et al. |
| 4,735,501 A | 4/1988 | Ginsburgh et al. |
| 4,787,369 A | 11/1988 | Allred, III et al. |
| 4,790,294 A | 12/1988 | Allred, III et al. |
| 4,794,912 A | 1/1989 | Lia |
| 4,796,607 A | 1/1989 | Allred, III et al. |
| 4,853,774 A | 8/1989 | Danna et al. |
| 4,862,253 A | 8/1989 | English et al. |
| 4,887,154 A | 12/1989 | Wawro et al. |
| 4,909,600 A | 3/1990 | Ciarlei et al. |
| 4,913,369 A | 4/1990 | Lia et al. |
| 4,941,454 A | 7/1990 | Wood et al. |
| 4,941,456 A | 7/1990 | Wood et al. |
| 4,962,751 A | 10/1990 | Krauter |
| 4,980,763 A | 12/1990 | Lia |
| 4,989,581 A | 2/1991 | Tamburrino et al. |
| 4,998,182 A | 3/1991 | Krauter et al. |
| 5,014,515 A | 5/1991 | Krauter |
| 5,014,600 A | 5/1991 | Krauter et al. |
| 5,018,436 A | 5/1991 | Evangelista et al. |
| 5,018,506 A | 5/1991 | Danna et al. |
| 5,019,121 A | 5/1991 | Krauter |
| 5,047,848 A | 9/1991 | Krauter |
| 5,052,803 A | 10/1991 | Krauter |
| 5,061,995 A | 10/1991 | Lia et al. |
| 5,066,122 A | 11/1991 | Krauter |
| 5,070,401 A | 12/1991 | Salvati et al. |

(Continued)

OTHER PUBLICATIONS

Zuo, Jon Z. et al, Combined Pulsating and Capillary Heat Pipe Mechanism for Cooling of High Heat Flux Electronics, 7 pages, BMDO SBIR contract DASG60-98-M-0123.

*Primary Examiner* — Le Luu

(74) *Attorney, Agent, or Firm* — GE Global Patent Operation; Mark A. Conklin

(57) ABSTRACT

Heat isolation and relocation systems and methods are provided to enable utilization of a remote viewing device in a wider range of temperature environments and while operating its one or more light sources at or near full power without fear of causing temperature-related harm to the one or more light sources and/or to the imager, even if the imager is positioned nearby the one or more light sources.

18 Claims, 2 Drawing Sheets

U.S. PATENT DOCUMENTS

| | | | |
|---|---|---|---|
| 5,114,636 A | 5/1992 | Evangelista et al. | |
| 5,140,975 A | 8/1992 | Krauter | |
| 5,191,879 A | 3/1993 | Krauter | |
| 5,202,758 A | 4/1993 | Tamburrino | |
| 5,203,319 A | 4/1993 | Danna et al. | |
| 5,275,152 A | 1/1994 | Krauter et al. | |
| 5,278,642 A | 1/1994 | Danna et al. | |
| 5,314,070 A | 5/1994 | Ciarlei | |
| 5,323,899 A | 6/1994 | Strom et al. | |
| 5,345,339 A | 9/1994 | Knieriem et al. | |
| 5,347,989 A | 9/1994 | Monroe et al. | |
| 5,365,331 A | 11/1994 | Tamburrino et al. | |
| 5,373,317 A | 12/1994 | Salvati et al. | |
| D358,471 S | 5/1995 | Cope et al. | |
| 5,435,296 A | 7/1995 | Vivenzio et al. | |
| 5,633,675 A | 5/1997 | Danna et al. | |
| 5,701,155 A | 12/1997 | Wood et al. | |
| 5,734,418 A | 3/1998 | Danna | |
| 5,754,313 A | 5/1998 | Pelchy et al. | |
| 5,857,963 A | 1/1999 | Pelchy et al. | |
| 6,083,152 A | 7/2000 | Strong | |
| 6,097,848 A | 8/2000 | Salvati | |
| 6,468,201 B1 | 10/2002 | Burdick | |
| 6,483,535 B1 | 11/2002 | Tamburrino et al. | |
| 6,494,739 B1 | 12/2002 | Vivenzio et al. | |
| 6,538,732 B1 | 3/2003 | Drost et al. | |
| 6,590,470 B1 | 7/2003 | Burdick | |
| 6,830,054 B1 | 12/2004 | Ross-Kuehn | |
| 6,950,343 B2 | 9/2005 | Takahashi | |
| 7,134,993 B2 | 11/2006 | Lia et al. | |
| 7,170,677 B1 | 1/2007 | Bendall et al. | |
| 2004/0183900 A1 | 9/2004 | Karpen et al. | |
| 2004/0215413 A1 | 10/2004 | Weldum et al. | |
| 2005/0050707 A1 | 3/2005 | Scott et al. | |
| 2005/0129108 A1 | 6/2005 | Bendall et al. | |
| 2005/0147289 A1* | 7/2005 | Kodama et al. | 382/152 |
| 2005/0162643 A1 | 7/2005 | Karpen | |
| 2005/0165275 A1 | 7/2005 | Von Felten et al. | |
| 2005/0205647 A1* | 9/2005 | Wang et al. | 228/102 |
| 2005/0222499 A1* | 10/2005 | Banik et al. | 600/132 |
| 2005/0281520 A1 | 12/2005 | Kehoskie et al. | |
| 2006/0050983 A1 | 3/2006 | Bendall et al. | |
| 2006/0072903 A1 | 4/2006 | Weldum et al. | |
| 2006/0200155 A1* | 9/2006 | Harp | 606/85 |
| 2007/0125962 A1* | 6/2007 | Okabe | 250/492.1 |
| 2008/0132760 A1* | 6/2008 | Takeuchi | 600/129 |
| 2009/0036739 A1* | 2/2009 | Hadani | 600/121 |
| 2009/0187077 A1* | 7/2009 | Hosoda et al. | 600/178 |

* cited by examiner

HEAT PROTECTION SYSTEMS AND METHODS FOR REMOTE VIEWING DEVICES

FIELD OF THE INVENTION

This invention relates generally to remote viewing devices, and, in particular, to systems and methods for protecting one or more temperature-sensitive components (e.g., one or more light sources, an imager) of a remote viewing device by isolating and/or relocating heat away from such components.

BACKGROUND OF THE INVENTION

A remote viewing device, such as an endoscope or a borescope, often is characterized as having an elongated and flexible insertion tube or probe with a viewing head assembly at its forward (i.e., distal) end, and a control section at its rear (i.e., proximal) end. Typically, the insertion tube is about 5 to 100 feet in length and approximately one-sixth to one-half inch in diameter, but it can have dimensions outside of these ranges as well. The viewing head assembly includes an optical tip and an imager, wherein at least one lens is spaced apart from, but is positioned relative to (e.g., axially aligned with) the imager. One or more light sources (e.g., one or more light emitting diodes) are disposed within the insertion tube, generally at or near the distal end thereof.

During use of a remote viewing device, image information is communicated from its viewing head assembly, through its insertion tube, and to its control section. In particular, light from the one or more light sources is transmitted out of viewing head assembly and, in return, image information representative of the inspection area is communicated to the imager (e.g., a CCD or CMOS camera assembly) via the at least one lens. This image information is processed and then outputted to a video monitor for viewing by an operator of the remote viewing device.

Different types of remote viewing devices generally are used for different purposes and in different settings. For example, an endoscope generally is used for remotely viewing the interior portions of a body cavity, such as for the purpose of medical diagnosis or treatment, whereas a borescope generally is used for remotely viewing interior portions of objects (e.g., industrial equipment, engines), such as for inspection purposes.

Certain parts of a remote viewing device are heat sensitive, such that they cease to function either entirely or at a satisfactory level if exposed to temperatures above a certain threshold. For example, light emitting diodes, which often act as the one or more light sources for a remote viewing device, can start to degrade and fail at temperatures above 120° C. Moreover, portions of the viewing head (e.g., the imager) of a remote viewing device likewise can begin to perform suboptimally at temperatures at or near 80° C., and can be vulnerable to failure at temperatures as low as about 10° C.

This can be problematic when, as is often the case, the one or more light sources are positioned near the imager of the remote viewing device. In general, operating the one or more light sources at or near full power will produce a high illumination output, and, in turn, beneficially will provide a more accurate image of the area being inspected by the remote viewing device. However, doing so also will cause the light source(s) to radiate heat, which can be at or above 100° when reaching the nearby imager. This creates a Catch-22 of sorts whereby one can operate the light source(s) at or near full power, thus obtaining advantageous results but risking damage to the nearby imager, or, instead, one can operate the light source(s) at less than full power, thus avoiding the potential to cause temperature-related harm to the imager but also ensuring that the obtained results will be suboptimal.

Another temperature-related problem can occur due to the usage environment of the remote viewing device. Whereas endoscopes tend to be utilized in settings at or near room temperature, borescopes often are employed in higher temperature usage environments, such as when performing inspections of aircraft engines or industrial equipment. If these inspections occur soon after the aircraft or equipment has finished its most recent operation, then the temperature environment being inspected can be well above the safe upper threshold of one or both of the at least one light source and the imager. This also creates a Catch-22 whereby one is forced either to wait to perform such inspections until the engine or equipment has definitely cooled below a temperature that could potentially harm the light source and/or the imager, thus disadvantageously requiring the aircraft or equipment to be non-operational during the waiting period, or, instead, to perform an inspection on a hot engine or piece of equipment, thus risking temperature-related harm to the light source and/or to the imager of the borescope.

Therefore, a need exists for systems and methods that would enable one to utilize a remote viewing device in a wider range of temperature environments and while operating its one or more light sources at or near full power without fear of causing temperature-related harm to the one or more light sources and/or to the imager, even if the imager is positioned nearby the one or more light sources.

SUMMARY OF THE INVENTION

These and other needs are met by an exemplary a remote viewing device comprising an insertion tube, at least one light source (e.g., one or more light emitting diodes) that is disposed within the insertion tube, an imager that is disposed within the insertion tube, and at least one heat protection element (e.g., one or more of a heat pipe, a heat relocation element and a thermal isolation element) that is disposed at a predetermined location (e.g., at least partially between the at least one light source and the image) within the insertion tube and that is effective to lower the temperature of at least one of the imager and the at least one light source.

Another exemplary remote viewing device comprises an insertion tube, at least one light source that is disposed within the insertion tube, an imager that is disposed proximate the at least one light source, wherein the imager has a predetermined upper temperature threshold, and at least one heat protection element that is disposed at a predetermined location within the insertion tube such that the at least one light source is operable at a temperature equal to at least the predetermined upper temperature threshold of the imager without causing temperature-related damage to the imager.

Yet another exemplary remote viewing device comprises an insertion tube, at least one light source that is disposed within the insertion tube, wherein each of the at least one light source has a predetermined upper temperature threshold, an imager that is disposed proximate the at least one light source, wherein the imager has a predetermined upper temperature threshold, and at least one heat protection element that is disposed at a predetermined location within the insertion tube such that the remote viewing device is operable in an environment having a temperature greater than at least one of the predetermined upper temperature threshold of the at least one light source and the predetermined upper temperature threshold of the imager without causing temperature-related damage to either of the at least one light source and the imager.

In accordance with any of these, and, if desired, other exemplary embodiments, the heat pipe, if present, can have a proximal end and a distal end, and the distal end can be connected to the at least one light source. Moreover, the heat relocation element, if present, can have a proximal end and a distal end, wherein the distal end of the heat relocation element can be attached to the heat pipe and the proximal end of the heat relocation element can be attached to the insertion tube. Also, the heat relocation element, if present, can be made of a low thermal resistance material, such as copper and/or its proximal end can be attached to the insertion tube at a location that is at least six inches away from the imager. Further, the thermal isolation element, if present, can be attached to the imager.

Still other aspect and embodiments, and the advantages thereof, are discussed in detail below. Moreover, it is to be understood that both the foregoing general description and the following detailed description are merely illustrative examples, and are intended to provide an overview or framework for understanding the nature and character of the invention as it is claimed. The accompanying drawings are included to provide a further understanding of the various embodiments described herein, and are incorporated in and constitute a part of this specification.

BRIEF DESCRIPTION OF THE DRAWINGS

For a further understanding of these and other aspects and embodiments of the present application, reference will be made to the following detailed description which is to be read in connection with the accompanying drawings, wherein.

DETAILED DESCRIPTION

Figure 1:
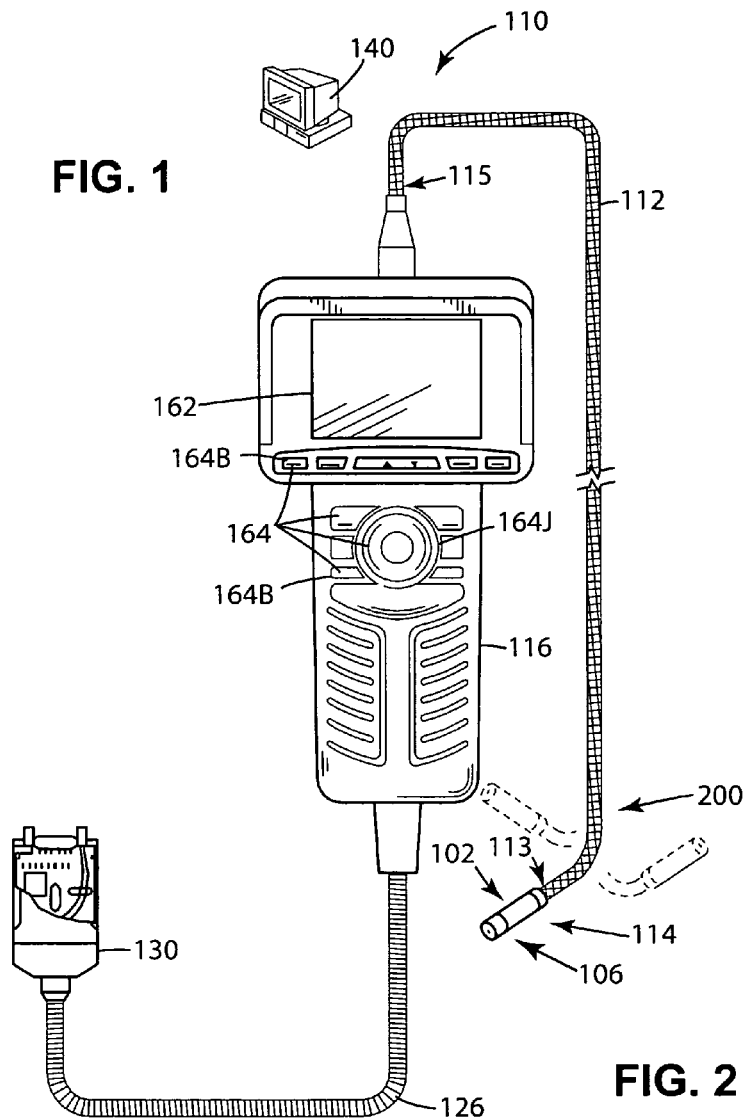
FIG. 1 illustrates an exemplary embodiment of a remote viewing device.
Figure 2:
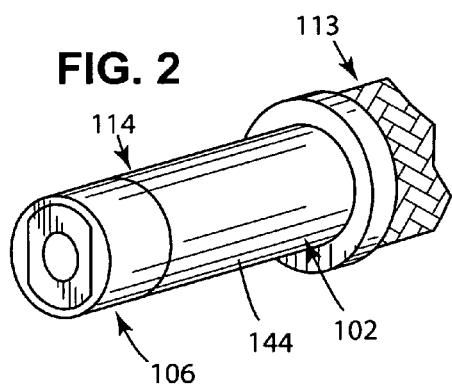
FIG. 2 illustrates an exemplary viewing head assembly for the remote viewing device of FIG. 1.
Figure 3:
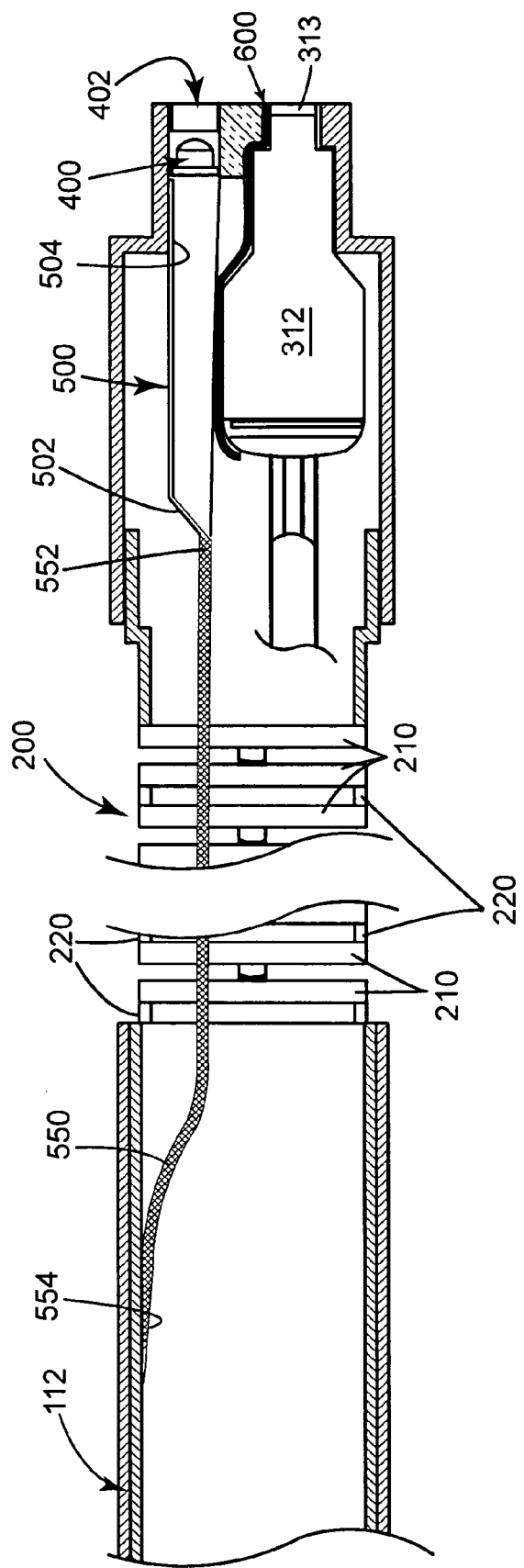
FIG. 3 illustrates a side, cross-sectional view of the insertion tube of the remote viewing device showing the presence of several elements for protecting one or more temperature-sensitive internal components of the remote viewing device of FIG. 1.

FIGS. 1-3 illustrate an exemplary embodiment of a remote viewing device 110 that includes a detachable optical tip 106 and a viewing head 102, each of which comprises a portion of a viewing head assembly 114. As best illustrated in FIGS. 2 and 3, the viewing head assembly 114 also includes a metal canister (can) 144 that surrounds an imager 312 and one or more associated lenses 313, which direct and focus incoming light towards the imager.

The remote viewing device 110 also includes various additional components, such as a power plug 130, an umbilical cord 126, a hand piece 116, and an insertion tube 112, each generally arranged as depicted in FIG. 1. The insertion tube 112 includes at least one articulation section 200 (see FIGS. 1 and 3) that is located comparatively closer to its distal end 113 than its proximal end 115.

The presence of the articulation section 200 enables an operator or other user of the remote viewing device 110 to control movement (e.g., bending) of the insertion tube 112 in various directions, e.g., as shown in phantom in FIG. 1. Such movement, as well as one or more other functions/operations of the remote viewing device 110, can be controlled via command inputs made using one or more controls 164 (e.g., buttons 164B and/or joystick 164J) on the hand piece 116.

To enable it to move and bend, the articulation section 200 of the insertion tube 112 generally has a construction that differs at least in part from the remainder of the insertion tube, which generally does not bend or move as such. By way of non-limiting example, and as illustrated in FIG. 3, the articulation section 200 can be formed of a plurality of washers 210 that are positioned and spaced apart from each other so as to allow for predetermined bending and/or movement of the articulation section. The articulation section 200 also includes a layer of a monocoil material 220 (as, generally, does the remainder of the insertion area 112) to provide crush resistance, yet also so as not to inhibit bending and movement as desired.

FIG. 2 illustrates an exemplary embodiment of the viewing head assembly 114 that includes a viewing head 102 and a detachable optical tip 106, such as those depicted in FIG. 1. As noted above, the viewing head 102 includes a metal canister 144, which encapsulates at least one lens 313 and an imager 312 (both shown in FIG. 3). The viewing head 102 generally also encloses elements of an image signal conditioning circuit (not shown). If desired, the viewing head 102 and the detachable optical tip 106 can include, respectively, threads (not shown) which enable the optical tip 106 to be threadedly attached and detached to the viewing head 102. It is understood, however, that other conventional fasteners can be substituted for such threads so as to readily provide for attachment and detachment of the optical tip 106 to and from the viewing head 114.

The detachable optical tip 106 also generally includes at least one lens (not shown) to receive incoming light from the area being inspected by the remote viewing device 110. Thus, when the tip 106 is attached to the viewing head 102 (e.g., via threading or fasteners), the one or more lenses associated with the tip 106 generally are disposed and aligned in series with the one or more lenses 313 associated with the imager 312, which can be, e.g., a CCD or CMOS camera assembly. In this instance, the term "associated" refers to the one or more lenses 313 being attached to and/or positioned relative to (e.g., axially aligned with) the imager 312.

It is understood that the detachable optical tip 106 can be replaced by one or more other detachable optical tips with differing operational characteristics, such as one or more of differing illumination, light re-direction, light focusing, and field/depth of view characteristics. Alternatively, different light focusing and/or field or depth of view characteristics can be implemented by attaching different lenses to different optical tips 106.

Although not shown, the metal can 144 generally also encapsulates an imager component circuit, which includes an image signal conditioning circuit and which is attached to a wiring cable bundle that extends through the insertion tube 112 to connect the viewing head 102 to the hand piece 116. By way of non-limiting example, the wiring cable bundle can pass through the hand piece 116 and the umbilical cord 126 to the power plug 130 of the remote viewing device 110. Alternatively, the wiring cable bundle can terminate in the hand piece 116. A continuous video image of the area being inspected by the remote viewing device 110 is displayed via the display 162 of the hand piece 116 and/or via a separate visual display monitor 140.

As noted above, the insertion tube 112 generally has a length in the range of about 5 feet to about 100 feet (including all subranges therebetween), wherein its length represents the distance between its distal end 113 and its proximal end 115. Moreover, the insertion tube 112 generally has a diameter in the range of about one-sixth of an inch to about one-half inch (including all subranges therebetween). It is understood, however, that the insertion tube 112 can have a length and/or a diameter outside of these (sub)ranges, if so desired. The specific length and diameter of the insertion tube 112 depend on various factors, such as the intended usage environment and/or the intended usage purpose of the remote viewing device 110.

Referring again to FIG. 3, the remote viewing device 110 further includes one or more light sources 400, each of which is disposed within the insertion tube 112 between the distal and proximal ends 113, 115 thereof. In an embodiment in which more than one light source 400 is present, any of the light sources can be of a different type than the other(s), can provide an additional amount of light output than the other(s), and/or can provide a light output having a different wavelength as compared to the other(s).

Generally, but not necessarily, each light source 400 is disposed comparatively closer to the distal end 113 of the insertion tube 112 than to the proximal end 115 thereof. By way of non-limiting example, and as shown in FIG. 3, each light source 400 can be disposed distal to the articulation section 200 of the insertion tube 112, wherein the distalmost light source includes a window 402 so as to allow light from the light source(s) to emanate from the remote viewing device 110 toward the area that is being inspected by the remote viewing device 110. Alternatively, the insertion tube 112 can include at least one light source 400 that is disposed distal to the articulation section 200 and at least another light source that is of the same or different type and that is disposed proximal to the articulation section yet distal to the proximal end 115 of the insertion tube.

The one or more light sources 400 can be any device(s) or object(s) suitably sized to fit within the insertion tube 112 and capable of projecting light to the surrounding environment (i.e., the inspection area) into which the remote viewing device 110 is placed. In accordance with a currently preferred yet still exemplary embodiment, the light source 400 is a light emitting diode (LED) or an array thereof. LEDs are a currently preferred light source 400 due to their efficiency, namely their high illumination output as compared to the modest power they require/consume.

When one or more LEDs are selected as the light source(s) 400, the color of each LED(s) can vary. Moreover, in an embodiment wherein the light sources 400 are an array of LEDs, the LEDs can be the same color or two or more different colors. By way of non-limiting example, each of the one or more light sources 400 can be a white LED. An exemplary LED is an LED die, such as is commercially available from Cree, Inc. of Durham, N.C. USA. Other suitable light sources 400 include, but are not limited to one or more arc discharge lamps (e.g., xenon, high pressure mercury, or metal halide lamps) of the type commercially available from Welch Allyn, Inc. of Skaneateles, N.Y. USA and/or one or more lasers (e.g., a white laser constructed from red, green and blue lasers).

In the FIGS. 1-3 exemplary embodiment, the light source 400 is an LED which is mechanically mounted within the metal can 144 and is positioned proximate (i.e., nearby) the imager 312. Based on this positioning, and as noted above, there can be concerns that the LED 400, when operated at or near full power, could radiate heat of a high enough temperature to harm the nearby imager 312, which, if so harmed, would either be rendered non-operational or would no longer be able to function optimally. This problem can be compounded, or at least made even more difficult to predict/control, if the usage environment (e.g., an aircraft engine or a piece of industrial equipment) of the remote viewing device 110 is one that can be hotter than the threshold temperature(s) that could cause damage to the LED 400 and/or to the imager 312.

FIG. 3 depicts several heat protection elements that individually and collectively solve these problems, wherein each heat protection element (a) enables heat to be separated from or relocated away from the light source 400 and/or the imager 312, and/or (b) thermally isolates the imager from heat that it would otherwise encounter due to, e.g., its proximity to the light source(s) 400. Among such heat protection element is at least one heat controlling element 500 that inhibits heat radiated from the light source(s) from reaching the imager 312. Thus, the presence of the heat controlling element 500 advantageously enables one to utilize the remote viewing device 110 under temperature conditions that normally would present a realistic risk of harm to the imager 312 due to its proximity to the light source(s), rather than disadvantageously not being able to use the remote viewing device to its fullest extent under such conditions.

By way of non-limiting example, and as shown in FIG. 3, the heat controlling element 500 can be a heat pipe having a generally cylindrical shape and being sized to fit within the insertion tube 112 at least partially in between the light source(s) 400 and the imager 312. The generally cylindrical shape of the heat pipe 500 is currently preferred due to ease of manufacturing; however, it is understood that the heat pipe can have other shapes if instead desired, such as in accordance with a different design preference and/or due to spatial limitations.

The heat pipe 500 has a proximal end 502 and a distal end 504 and is maintained in place by being connected to at least one of the one or more light sources 400. The proximal end 502 of the heat pipe 500 is located distal to the articulation section 200 of the insertion tube 112, so as to avoid causing damage to the heat pipe in connection with the bending or movement of the articulation section.

The specific connection between the heat pipe 500 and the light source(s) 400 can vary; however, by way of non-limiting example and in accordance with the embodiment shown in FIG. 3, the presence of the light source(s) can define a bore (not shown) into which the distal end 504 of the heat pipe 500 can be secured while in contact with the light source(s) without obstructing the window 402 of the light source(s) 400. By virtue of this placement, the temperature at the distal end 504 of the heat pipe 500 generally will be higher than it is at the proximal end 502, since the distal end is comparatively closer to the heat radiating light source(s) 400.

If desired, a predetermined quantity of an epoxy or other adhesive can be added within the bore and/or onto the distal end 504 of the heat pipe 500 so as to create a more secure connection or bond between the light source(s) 400 and the heat pipe. However, if an epoxy/adhesive is present as such, it is currently preferred that the epoxy/adhesive provide low thermal resistance so as not to interfere with the heat controlling purpose of the heat pipe 500.

The heat pipe 500 encloses a predetermined quantity of liquid (not shown), at least some of which will be located at or near the distal end 504 of the heat pipe 500 during use of the remote viewing device 110. If the temperature of the distal end 504 of the heat pipe 500 (or any other portion thereof) exceeds the boiling point of the enclosed liquid, then the liquid will be caused to boil, thus turning the enclosed liquid into a vapor, which is automatically directed toward the comparatively lower temperature proximal end 502 of the heat pipe. The vapor cools over time and eventually condenses so as to lower the temperature of the heat pipe 500—including at its distal end 504—below the predetermined temperature that initially caused the liquid to boil. If, following this cooling, the temperature environment in which the heat pipe 500 is placed exceeds this predetermined temperature, then the liquid will caused to re-boil, thus commencing the boiling, vaporizing and cooling cycle anew. This cycle can be repeated continuously, since the quantity of liquid contained within the heat pipe 500 is maintained during the entirety of the cycle.

The predetermined temperature at which the liquid in the heat pipe 500 begins to boil can be tailored by selecting a liquid having a known boiling point. Thus, where, as here, it is important not to exceed one or more temperature thresholds, one can select the liquid within the heat pipe 500 to ensure that the boiling, vaporizing and cooling cycle occurs prior to each of one or more a predetermined temperature thresholds being reached.

As such, by placing the heat pipe 500 between the one or more light sources 400 and the imager 312 (as illustrated, for example, in FIG. 3), one can safely operate the one or more light sources at a higher output power than could normally occur without fear of causing harm to the imager due to the heat radiated by the one or more light sources, since the presence of the heat pipe acts as a impediment for heat radiated by the one or more light sources that would normally reach—and could potentially harm—the nearby imager. In other words, the heat pipe 500 can be designed (e.g., based on selecting the liquid contained therein) such that the boiling, vaporizing and cooling cycle of the heat pipe will take effect at a predetermined temperature that is below the threshold temperature of the imager 312.

As an added guard against temperature-related damage being caused to the imager 312 (e.g., via heat radiated from the light source(s) 400), at least one additional heat protection element, in the form of one or more heat relocation elements 550, can be provided. The positioning and/or the composition of the heat relocation element 550 is effective to cause at least some of the heat encountered by the heat pipe 500 (e.g., from the light source(s)) to be relocated away from the heat pipe.

In an embodiment of the remote viewing device 110 that includes the heat relocation element 550, the heat pipe 500 can further include a wick (not shown). When included, the wick generally is formed of a heat-conductive metal material so as to improve the heat transfer capability of the heat pipe 500. It should be noted, however, that the heat pipe 500 also can include a wick in embodiments that do not include the heat relocation element 550.

The heat relocation element 550 can be connected to the heat pipe 500. As shown in the exemplary embodiment of FIG. 3, the heat relocation element 550 is attached to the proximal end 502 of the heat pipe 500 in the form of a quantity of low thermal resistance material, such as copper braid or wire. Specifically, the distal end 552 of the copper braid 550 is attached (e.g., bonded) to the proximal end of the heat pipe 500 and its proximal end 554 is attached (e.g., bonded) to the insertion tube 112 at a location away from the imager 312 and the light source(s) 400. By way of non-limiting example, and as shown in FIG. 3, the proximal end 554 of the copper braid 550 can be attached to the insertion tube (e.g., to the monocoil layer thereof) at a location proximal to the articulation section 200 of the insertion tube 112.

Due to its low thermal resistance, the heat relocation element 550 functions to remove heat that comes in contact therewith. Thus, heat from the heat pipe 500 travels from the distal end 552 of the heat relocation element 550 that is in contact with the heat pipe to the proximal end 554 that is in contact with the insertion tube 112. Accordingly, the presence of the heat relocation element 550 serves to keep the heat pipe 500 cooler for a comparatively longer period of time than if the heat relocation element was not present. That, in turn, enables the heat pipe 500 to even more reliably shield the imager 312 from heat radiated by the light source(s) 400.

The attachment location of the proximal end 554 of the heat relocation element 550 generally will depend on the specific material from which the heat pipe 500 is made as well as the measured/anticipated temperature of the heat upon reaching the attachment location, wherein the attachment location will need to be far enough from the imager 312 that the relocated heat cannot harm the imager even if above its temperature threshold. In accordance with an exemplary embodiment in which the heat relocation element 550 is a copper braid, the attachment location of the proximal end 554 of the heat relocation element 550 is in the range of about six inches to about eighteen inches (includes all subranges in between) away from the imager 312.

It should be noted that although not shown in the FIG. 3 exemplary embodiment, the remote viewing device 110 can include a heat relocation element 550 even if a heat controlling element 500 is not present. In accordance with such an alternative embodiment, the distal end 552 of the heat relocation element 550 can be connected (e.g., bonded) to the light source 400 and the proximal end 554 of the heat relocation element 550 can be attached to an attachment location that is suitably proximal to the imager 312.

To provide further or separate assurance that the imager 312 will not be damaged via heat radiated from the light source(s), the remote viewing device 110 can include yet another heat protection element in addition to or in lieu of the heat pipe 500 and the attached heat relocation element 550. For example, the light source(s) 400 and the imager 312 can be thermally isolated from one another by a heat protection, as can be, therefore, the illumination path of the light source(s) and the imaging path of the imager.

This thermal isolation can be accomplished, for example, by including at least one thermal isolation element 600 as a heat protected element, wherein the thermal isolation element 600 is placed at least partially in between the light source(s) 400 and the imager 312. An exemplary thermal isolation element 600 is shown in FIG. 3 as a quantity of (e.g., a blanket of) thermal insulating material, which, by virtue of its placement, acts as complete or partial a physical barrier between the one or more light sources 400 and the imager 312, yet does not interfere with the imaging path of the imager or the illumination path of the light source(s).

The thermal isolation element 600 can be physically connected to the imager 312, such as through the use of an epoxy, an adhesive or a fiberglass tape. Alternatively, the thermal isolation element 600 can be draped over, but not physically connected to the imager 312. Generally, however, it is currently preferred to physically connect the thermal isolation element 600 to the imager 312 due to the potential that a non-connected thermal isolation element could be shifted from its intended placement location as the insertion tube 112 is moved during routine use of the remote viewing device 110.

The specific material from which the thermal isolation element is made can vary, as can its specific length and thickness. These choices generally are made based on one or more of several factors, such as the specific temperature threshold of the imager 312, whether the heat controlling element 500 is present (and, if so, whether the heat relocation element 550 is present as well), the temperature at which the one or more light sources 400 are to be operated, and/or the temperature environment in which remote viewing device 110 is to be used.

Thus, the presence of one or more heat protection elements (i.e., the one or more thermal insulating element 600, heat controlling element 500 and heat relocation element 550) can provide individual and collective assurance that heat radiated from the light source(s) 400 will be inhibited from reaching the imager 312, or, alternatively, that such heat will reach the imager at a lower temperature than would otherwise be the case, wherein this lower temperature is below the upper temperature threshold of the imager. That, in turn, enables one to operate the light source (s) at or very near full power output without fear of causing temperature-related harm to the imager 312.

This is advantageous in general, but particularly in an instance where the one or more light source(s) 400 are LEDs, since their operating temperature at full power can be, in certain instances, only about 20° C. higher than the temperature threshold of the imager 312. Accordingly, the presence of the one or more heat protection elements provides assurance that the temperature of the heat radiated from the light source(s) 400 would be below this threshold if/when reaching imager 312.

As further noted above, however, the imager 312 can be harmed not only by heat from operation of the light source (s) 400. For example, the imager 312 and/or the light source(s) 400 can be harmed if the remote viewing device 110 is used to inspect an area that has a temperature above either or both of their respective thresholds, as can occur, e.g., when inspecting a recently used aircraft engine or industrial component. Under such circumstances, necessary adjustments can be made to accommodate the potential for such added temperature, wherein such adjustments can include, but are not limited to, adding one or more additional heat protection elements, changing the liquid within the heat controlling element 500 (if present or added), changing the thickness, length and/or material of the thermal isolation element 600 (if present or added), and/or changing the location and/or material of the low thermal resistance element 550 (if present or added).

Although various embodiments have been described herein, it is not intended that such embodiments be regarded as limiting the scope of the disclosure, except as and to the extent that they are included in the following claims—that is, the foregoing description is merely illustrative, and it should be understood that variations and modifications can be effected without departing from the scope or spirit of the various embodiments as set forth in the following claims. Moreover, any document(s) mentioned herein are incorporated by reference in its/their entirety, as are any other documents that are referenced within such document(s).

What is claimed is:

1. A remote viewing device, comprising:
   an insertion tube;
   at least one light source disposed within the insertion tube;
   an imager disposed within the insertion tube; and
   at least one heat protection element disposed at a predetermined location within the insertion tube and being effective to lower the temperature of the imager and the at least one light source,
   wherein the at least one heat protection element comprises,
      a heat pipe coupled to the light source, the heat pipe comprising a cylindrical tube configured to hold liquid that vaporizes to remove heat generated by the light source; and
      a braid coupled to the heat pipe and the insertion tube at a location away from the imager and the light source.

2. The remote viewing device of claim 1, wherein the predetermined location of the at least one heat protection element is at least partially in between the at least one light source and the imager.

3. The remote viewing device of claim 1, wherein the predetermined location of the cylindrical tube is at least partially in between the at least one light source and the imager.

4. The remote viewing device of claim 1, wherein the braid comprises copper.

5. The remote viewing device of claim 1, wherein the proximal end of the braid is attached to the insertion tube at a location that is at least six inches away from the imager.

6. The remote viewing device of claim 1, wherein the at least one heat protection element is comprises a thermal isolation element.

7. The remote viewing device of claim 6, wherein the thermal isolation element is attached to the imager.

8. The remote viewing device of claim 6, wherein the predetermined location of the thermal isolation element is at least partially in between the at least one light source and the imager.

9. The remote viewing device of claim 1, wherein the at least one light source comprises a light emitting diode.

10. A remote viewing device, comprising:
    an insertion tube;
    at least one light source disposed within the insertion tube;
    an imager disposed proximate the light source, wherein the imager has a predetermined upper temperature threshold;
    a heat pipe comprising a cylindrical tube coupled to the light source disposed at a predetermined location within the insertion tube such that the light source is operable at a temperature equal to at least the predetermined upper temperature threshold of the imager without causing temperature-related damage to the imager; and
    a copper braid coupled to the heat pipe and to the insertion tube at a location way from the imager.

11. The remote viewing device of claim 10, wherein the predetermined location of the heat pipe is at least partially in between the at least one light source and the imager.

12. The remote viewing device of claim 10, wherein each of the at least one light source comprises a light emitting diode.

13. The remote viewing device of claim 10, further comprising a thermal isolation element attached to the imager.

14. A remote viewing device, comprising:
    an insertion tube;
    at least one light source disposed within the insertion tube, wherein the light source has a predetermined upper temperature threshold;
    an imager disposed proximate the at least one light source, wherein the imager has a predetermined upper temperature threshold; and
    a heat protection element comprising a heat pipe comprising a cylindrical tube coupled to the light source and a braid coupled to the heat pipe and the insertion tube at a location away from the imager and the light source,
    wherein the heat protection element is disposed at a predetermined location within the insertion tube such that the remote viewing device is operable in an environment having a temperature greater than at least one of the predetermined upper temperature threshold of the light source and the predetermined upper temperature threshold of the imager without causing temperature-related damage to either of the light source and the imager.

15. The remote viewing device of claim 14, wherein the predetermined location of the heat protection element is at least partially in between the at least one light source and the imager.

16. The remote viewing device of claim 14, wherein the at least one light source comprises a light emitting diode.

17. The remote viewing device of claim 14, wherein the heat protection element further comprises a thermal isolation element.

18. The remote viewing device of claim 17, wherein the thermal isolation element is attached to the imager.

* * * * *